(12) United States Patent
Garwood et al.

(10) Patent No.: US 9,320,452 B2
(45) Date of Patent: Apr. 26, 2016

(54) MAGNETIC RESONANCE IMAGING OF AMYLOID PLAQUE IN THE BRAIN

(75) Inventors: Michael G. Garwood, Medina, MN (US); Clifford R. Jack, Jr., Rochester, MN (US); Joseph F Podusло, Rochester, MN (US); Thomas M. Wengenack, Rochester, MN (US)

(73) Assignees: MAYO FOUNDATION FOR MEDICAL EDUCATION AND RESEARCH, Rochester, MN (US); REGENTS OF THE UNIVERSITY OF MINNESOTA, St. Paul, MI (US)

( * ) Notice: Subject to any disclaimer, the term of this patent is extended or adjusted under 35 U.S.C. 154(b) by 2942 days.

(21) Appl. No.: 11/631,581

(22) PCT Filed: Jun. 28, 2005

(86) PCT No.: PCT/US2005/022872
§ 371 (c)(1),
(2), (4) Date: Jan. 23, 2008

(87) PCT Pub. No.: WO2006/014260
PCT Pub. Date: Feb. 9, 2006

(65) Prior Publication Data
US 2008/0262339 A1    Oct. 23, 2008

Related U.S. Application Data
(60) Provisional application No. 60/585,691, filed on Jul. 6, 2004.

(51) Int. Cl.
*A61B 5/055* (2006.01)
*A61B 5/00* (2006.01)
*G01R 33/567* (2006.01)

(52) U.S. Cl.
CPC ............... *A61B 5/055* (2013.01); *A61B 5/7285* (2013.01); *G01R 33/5673* (2013.01); *A61B 5/4088* (2013.01)

(58) Field of Classification Search
CPC .... A61B 5/055; A61B 5/4088; A61B 5/7285; G01R 33/5673
USPC .......................... 600/407, 410, 413, 425, 428
See application file for complete search history.

(56) References Cited

U.S. PATENT DOCUMENTS

| 4,777,957 A | 10/1988 | Wehrli et al. |
| 4,988,947 A | 1/1991 | Ugurbil et al. |
| 5,908,386 A | 6/1999 | Uburbil et al. |
| 6,068,595 A * | 5/2000 | Miyazaki et al. ............. 600/410 |
| 6,144,201 A | 11/2000 | Miyazaki |
| 6,292,684 B1 | 9/2001 | Du et al. |
| 6,650,116 B2 | 11/2003 | Garwood et al. |

OTHER PUBLICATIONS

International Search Report and Written Opinion corresponding to PCT/US2005/022872, under date of mailing of Aug. 18, 2006.

* cited by examiner

*Primary Examiner* — Mark Remaly
(74) *Attorney, Agent, or Firm* — Quarles & Brady, LLP (57) ABSTRACT

Amyloid plaque in the brain of a subject is imaged in an MRI system with or without the use of a contrast agent. Contrast is achieved using a spin-echo pulse sequence that is both respiratory gated and cardiac gated to reduce motion artifacts at the very high image resolution required to see plaque. A preparatory pulse sequence is used to insure longitudinal magnetization remains constant for all the acquired views even if the effective TR changes during the scan due to irregular breathing.

11 Claims, 5 Drawing Sheets

MAGNETIC RESONANCE IMAGING OF AMYLOID PLAQUE IN THE BRAIN

CROSS-REFERENCE TO RELATED APPLICATIONS

This application is based on U.S. Provisional patent application Ser. No. 60/585,691 filed on Jul. 6, 2004 and entitled "In Vivo Visualization of Alzheimer's Amyloid Plaques by MRI in Transgenic Mice Without a Contrast Agent".

STATEMENT REGARDING FEDERALLY SPONSORED RESEARCH

This invention was made with government support under Grant No. AG022034 and RR008079 awarded by the National Institute of Health. The United States Government has certain rights in this invention.

BACKGROUND OF THE INVENTION

The field of the invention is nuclear magnetic resonance imaging methods and systems. More particularly, the invention relates to the imaging of amyloid plaques in subjects with Alzheimer's disease.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned longitudinal magnetization $M_z$, may be rotated, or "tipped", into the x-y plane to produce a net transverse magnetization $M_t$. A signal is emitted by the excited spins after the excitation signal $B_1$ is terminated, this signal may be received and processed to form an image.

When utilizing these signals to produce images, magnetic field gradients ($G_x$, $G_y$ and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

The present invention will be described in detail with reference to a variant of the well known Fourier transform (FT) imaging technique, which is frequently referred to as "spin-warp". The spin-warp technique is discussed in an article entitled "Spin-Warp NMR Imaging and Applications to Human Whole-Body Imaging" by W. A. Edelstein et al., Physics in Medicine and Biology, Vol. 25, pp. 751-756 (1980). It employs a variable amplitude phase encoding magnetic field gradient pulse prior to the acquisition of NMR spin-echo signals to phase encode spatial information in the direction of this gradient. In a two-dimensional implementation (2DFT), for example, spatial information is encoded in one direction by applying a phase encoding gradient ($G_y$) along that direction, and then a spin-echo signal is acquired in the presence of a readout magnetic field gradient ($G_x$) in a direction orthogonal to the phase encoding direction. The readout gradient present during the spin-echo acquisition encodes spatial information in the orthogonal direction. In a typical 2DFT pulse sequence, the magnitude of the phase encoding gradient pulse $G_y$ is incremented in the sequence of views that are acquired during the scan to produce a set of NMR data from which an entire image can be reconstructed.

Alzheimer's disease (AD) is a slowly progressive neurodegenerative disorder with an insidious clinical onset. Above 65 years of age, AD increases in incidence exponentially with age and is therefore poised to become a leading public health problem as the population ages. At this time, no diagnostic biomarker exists. The antemortem diagnosis as well as longitudinal assessment of disease progression are based on clinical and neuropsychometric measures. Due to the anticipated arrival of useful therapeutic interventions for AD, improved methods of diagnosis and measures of disease progression are needed.

Recent evidence in genetics and cell biology have led to general acceptance that the initiating event ultimately leading to clinical AD is disordered metabolism of amyloid in the brain. Amyloid precursor protein (APP) is a normal transmembrane protein found in cells throughout the body. Amyloid β peptide (Aβ) is one of the products of normal metabolic turnover of APP in the brain. Aβ is a major component of extracellular senile (or amyloid) plaques, and, aggregation of extracellular Aβ fragments is thought to be the initiating event in plaque formation. Soluble Aβ polymers are neurotoxic. While plaques themselves may or may not be directly neurotoxic, plaque burden is a measure of the antecedent biochemical events ultimately leading to clinical AD.

The three known types of mutations associated with early onset, familial AD all directly effect amyloid metabolism. Murine models of AD have been created by inserting one or more human mutations into the mouse genome. These transgenic mice display extensive plaque formation, whereas plaques are not found in wild type mice. Amyloid reduction in humans has recently been identified as a major therapeutic objective. Alzheimer's transgenic mice allow controlled study of this phenomenon and enable testing of anti-amyloid interventions that might be useful in humans.

Direct imaging of amyloid in the brain is feasible. Plaque binding scintigraphic probes label plaques in animal and human specimens in vitro, and in vivo in mice. Plaque burden has successfully been visualized with position emission tomography (PET) in living human Alzheimer's patients using the "Pittsburgh" compound. Optical imaging of individual probe labeled plaques has also been demonstrated. Despite this success with other modalities, several groups have pursued imaging of amyloid plaques with MRI. A major motivation for this effort is that, unlike other modalities, MRI theoretically can resolve individual plaques noninvasively. Typical plaques in human AD subjects range from 2 to 200 μm in diameter which is beyond the spatial resolution of PET.

Benvineste, et al. in "Detection of neuritic plaques in Alzheimer's disease by magnetic resonance microscopy," Proceedings of the National Academy of Sciences of the Untied States of America 1999; 96(24):14079-14084, demonstrated individual plaques on in vitro human tissue slices using MR microscopy. This was accomplished at 7 T at a spatial resolution in the range of 40 μm×40 μm×40 μm (~6× $10^{-5}$ mm$^3$). Plaques appeared dark on $T_2$*-weighted images and this was attributed to the known presence of metals, particularly iron, in plaques. However, Poduslo, et al, demonstrated in "Molecular Targeting Of Alzheimer's Amyloid Plaques For Contrast-Enhanced Magnetic Resonance Imaging," Neurobiology of Disease 2002, 11:315-329, that imaging of plaques in ex vivo transgenic mouse brain specimens at 7 T without administration of an exogenous contrast agent on $T_2$-weighted images could be achieved. Poduslo, et al. also demonstrated enhancement of plaques ex vivo both on $T_2$ and $T_1$-weighted images following IV administration of a specifically designed molecular contrast agent. However, imaging times in these experiments ranged from 13-15 hours which is clearly unsuitable for in vivo imaging.

SUMMARY OF THE INVENTION

The present invention is a method for acquiring very high resolution in vivo images of a subject using respiratory gating. Each pulse sequence in the image acquisition is triggered by a signal from a physiological monitor which detects a specific point in the respiratory cycle, and a preparatory pulse sequence precedes each imaging pulse sequence to create uniform view-to-view longitudinal magnetization in the presence of non-uniform view-to-view respiratory trigger times.

Another aspect of the invention is a method for both respiratory and cardiac triggering of the image acquisition to minimize motion artifacts. The respiratory trigger signal triggers execution of the preparatory pulse sequence to properly prepare longitudinal magnetization and the cardiac signal triggers the execution of the imaging pulse sequence.

Another aspect of the present invention is a magnetic resonance imaging method for in vivo imaging amyloid plaque in the brain of a subject without using a contrast agent. A very high resolution spin-echo imaging pulse sequence is employed to acquire data from which an image is reconstructed.

Another aspect of the invention is to acquire very high resolution MR images of the brain in clinically useful scan times. In addition to the use of a very high polarizing magnetic field strength, a zoom imaging step is employed to reduce the number of views that need to be acquired. A very high resolution image from a relatively small region of interest in the subject's brain is thus acquired without artifacts being aliased into the image from surrounding tissues.

DESCRIPTION OF THE PREFERRED EMBODIMENTS

Initial in vivo imaging of amyloid plaque was performed on transgenic mice using a very high field strength magnetic resonance imaging system. Scans were performed with a spectrometer sold under the trademark "Unity Inova" by Varian of Palo Alto, Calif., interfaced with a 9.4 Tesla horizontal bore magnet commercially available from Magnex Scientific of Abingdon, U.K. The magnet is equipped with actively-shielded gradients capable of 300 mT/m in a rise-time of 500 µs. The magnet bore is 31 cm in diameter and RF excitation and NMR signal reception is done using 1 cm quadrature surface coils.

Figure 3:
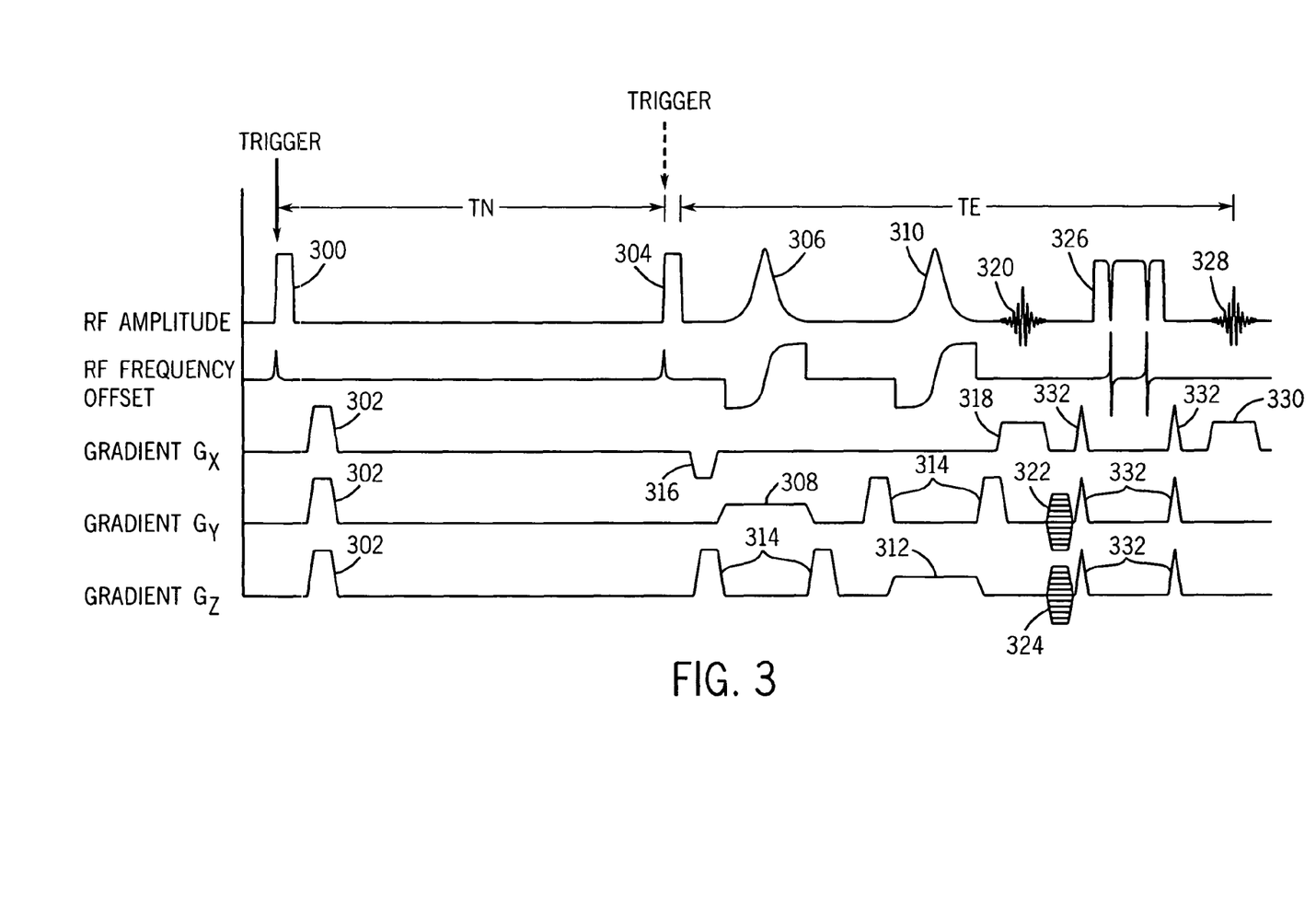
FIG. 3 is a graphic representation of a preferred pulse sequence employed in an MRI system to practice the present invention.

Referring particularly to FIG. 3, the pulse sequence employed in this MRI system to acquire image data is initiated by a first trigger signal produced by a respiration monitor. The first trigger signal is generated when the subject reaches a preselected phase of the respiratory cycle to insure that each view is acquired at the same point, or respiratory phase of the respiration cycle. Precision is required in this application due to the extremely high image resolution that is needed to see amyloid plaque deposits.

Because respiratory trigger signals do not necessarily occur at regular intervals due to normal, non-uniformity in breathing patterns, the longitudinal magnetization is prepared by first applying a non-selective RF nulling pulse 300. This is an adiabatic half-passage RF pulse that has a 90° flip angle that sets the longitudinal magnetization to substantially zero by tipping the magnetization to the transverse plane. The resulting transverse magnetization is immediately dephased by spoiler gradients 302 produced on all three gradient axes. After a null recovery time (TN) which is long enough to allow the longitudinal magnetization to recover to a selected level, this preparatory pulse sequence is completed and the imaging pulse sequence begins. As a result of the preparatory or nulling pulse sequence, the longitudinal magnetization is substantially at the same level for each view acquisition regardless of the variations that may occur in respiratory gating due to irregular subject breathing. The "selected level" is chosen to be the same longitudinal magnetization that would occur if the pulse sequence were repeated at a prescribed TR interval.

The imaging pulse sequence is a double spin echo pulse sequence that begins with a non-selective RF excitation pulse 304. It is an adiabatic half-passage RF pulse with a substantially 90° flip angle. Most MRI methods scan an entire organ or anatomic region of interest. However, in order to achieve the spatial resolution necessary to visualize individual plaques in a reasonable scan time for in vivo imaging, an alternative approach is employed. Significant scan time reduction can be achieved by restricting the volume of the brain that is imaged. This is achieved using the "zoom imaging" method described by Grohn, et al. "Adiabatic Inner Volume Selection (IVS) Method For High Resolution 3D MRI" Proc Interl Soc Mag Reson Med 2003:11:960.

More specifically, a first slice-selective 180° RF refocusing pulse 306 is applied in the presence of a gradient pulse 308 directed along the phase encoding gradient axis $G_y$, and a second slice-selective 180° RF refocusing pulse 310 is applied in the presence of a gradient pulse 312 directed along the second phase encoding gradient axis $G_z$. The refocusing pulses 306 and 310 are of the hyperbolic secant type and are 2 ms in duration and have a 10 kHz bandwidth. The refocusing pulses 306 and 310 and their respective slice selection gradient pulses 308 and 312 refocus and refocus the spin magnetization in a selected region of the subject's brain where amyloid plaque is to be imaged. Typically this is the allocortex and neocortex of the brain in mice and in humans. Gradient pulses 314 serve as spoilers that dephase any transverse magnetization outside this selected region that results during the double refocusing process.

Two NMR echo signals are acquired during the performance of this pulse sequence. The transverse magnetization produced by RF excitation pulse 304 is dephased by an initial readout gradient dephasing pulse 316 and is then resphased by a readout gradient pulse 318 to produce a navigator NMR echo signal 320. As described in U.S. Pat. No. 4,937,526, the navigation NMR echo signal 320 is not phase encoded and is used to detect view-to-view subject motion and enable correction of such motion as will be described in more detail below. Following this readout, the transverse magnetization is phase encoded with phase encoding gradient pulses 322 and 324 directed along the respective phase encoding gradient axes $G_y$ and $G_z$. As is well known in the art, these phase encodings are stepped through a series of prescribed values during the scan to acquire image data over the prescribed field of view and prescribed image resolution.

Following phase encoding, a non-selective, 180° RF refocusing pulse 326 is applied to produce a spin-echo NMR signal 328 at the prescribed echo time (TE). This spin-echo NMR signal 328 is acquired in the presence of a readout gradient pulse 330 to frequency encode the sampled signal along readout gradient axis $G_x$. The refocusing pulse 326 is a BIR4 pulse of the type described by Garwood, et al., "Symmetric Pulses to Induce Arbitrary Flip Angles with Compensation for RF Inhomogeneity and Resonance Offsets," *Journal of Magnetic Resonance* 1991; 94:511-525, and it has a duration of 2 ms. Spoiler gradient pulses 332 are produced along all three gradient axes $G_x$, $G_y$, and $G_z$ to dephase unwanted transverse magnetization before signal readout. This pulse sequence is repeated as necessary to acquire the number of views needed to sample k-space in the prescribed manner.

Although it is possible to artificially ventilate the subject and thereby regulate breathing, in the first preferred embodiment, the repetition of the pulse sequence is governed by respiratory triggering. In the high field system using mice as subjects, we employ an MR compatible physiologic monitoring device for these experiments (SA Instruments, Inc.). Respiration is monitored using a pressure transducer placed under the mouse's abdomen and triggering signals are derived from this transducer.

Acquisition bandwidth and TE is empirically adjusted to optimize SNR and contrast for plaque visualization using ex vivo fixed brain specimens from transgenic mice. Preferred pulse sequence parameters are: TR=2000 ms; TE=52 ms; bandwidth=44 kHz; x, y, and z matrices of 256×64×32 with FOV of 15.36 mm in x and 3.84 mm in y. Accordingly, in-plane voxel dimensions are 60×60 µm. Through-plane resolution is optimized by assessing plaque conspicuity at varying z FOV corresponding to slice thickness ranging from 60 to 270 µm. While plaque sharpness was best resolved at 60 µm, SNR is problematic at this high resolution and 120 µm is preferred for mice as a compromise. Data acquired with the spin echo sequence outlined above has been compared to a 3D gradient recalled $T_2^*$ weighted sequence. The $T_2^*$ weighted sequence parameters are, TR=150 ms, TE=16.4 ms, nominal flip angle=15 degrees, bandwidth=60 kHz; x, y, and z matrices of 256×256×128 with FOV of 15.4 mm in all three dimensions. Accordingly, voxel dimensions are 60 µm×60 µm in plane and 120 µm through-plane (identical to those of the preferred spin echo sequence). Imaging time is 1 hr 8 minutes for the preferred spin echo sequence.

These scan parameters will, of course, differ depending on the subject of the scan and the particular MRI system used. One important variable in this clinical application is the field strength of the polarizing magnet. Higher field strengths enable higher SNR signals to be acquired from the very small voxels needed to resolve amyloid plaque. To acquire images of the same resolution using lower field strengths (e.g. 3 Tesla) multi-NEX acquisitions are performed in which each phase encoding view is acquired two or more times and the acquired data is averaged to increase SNR. The tradeoff is between increased scan time and lower field strength.

The Navigator data may be acquired with the preferred pulse sequence and this is used to correct minor view-to-view phase inconsistency still present despite the use of physiological triggering and the trigger desensitizing preparatory pulse sequence. Navigator data is processed by performing a 1D Fourier transformation along the readout direction of the navigator echo signal 320. Both a pixel shift (δ) due to bulk subject motion and a DC phase term (θ) due to physiologic motion is determined. The pixel shift is determined by minimizing the squared difference of the navigator signal magnitude relative to a reference navigator signal magnitude. A magnitude weighted least square fit of the phase term is used to determine the DC phase term. The correction to the sampled data becomes:

$$s'(k_x)=s(k_x)e^{-i\theta}e^{-i2\pi\delta k_x/256},\text{ where } k_x \text{ is the } x^{th} \text{ point in k-space.}$$

The execution of pulse sequence of FIG. 3 may be modified to accept a second trigger signal. In the preferred embodiment cardiac gating is employed to insure the imaging pulse sequence is performed at the same phase (preferably diastole) in the subject's cardiac cycle from view-to-view. An electrocardiography (ECG) monitoring device is employed to produce the second trigger signal which is produced after each detected QRS complex at the prescribed cardiac phase.

Figure 5:
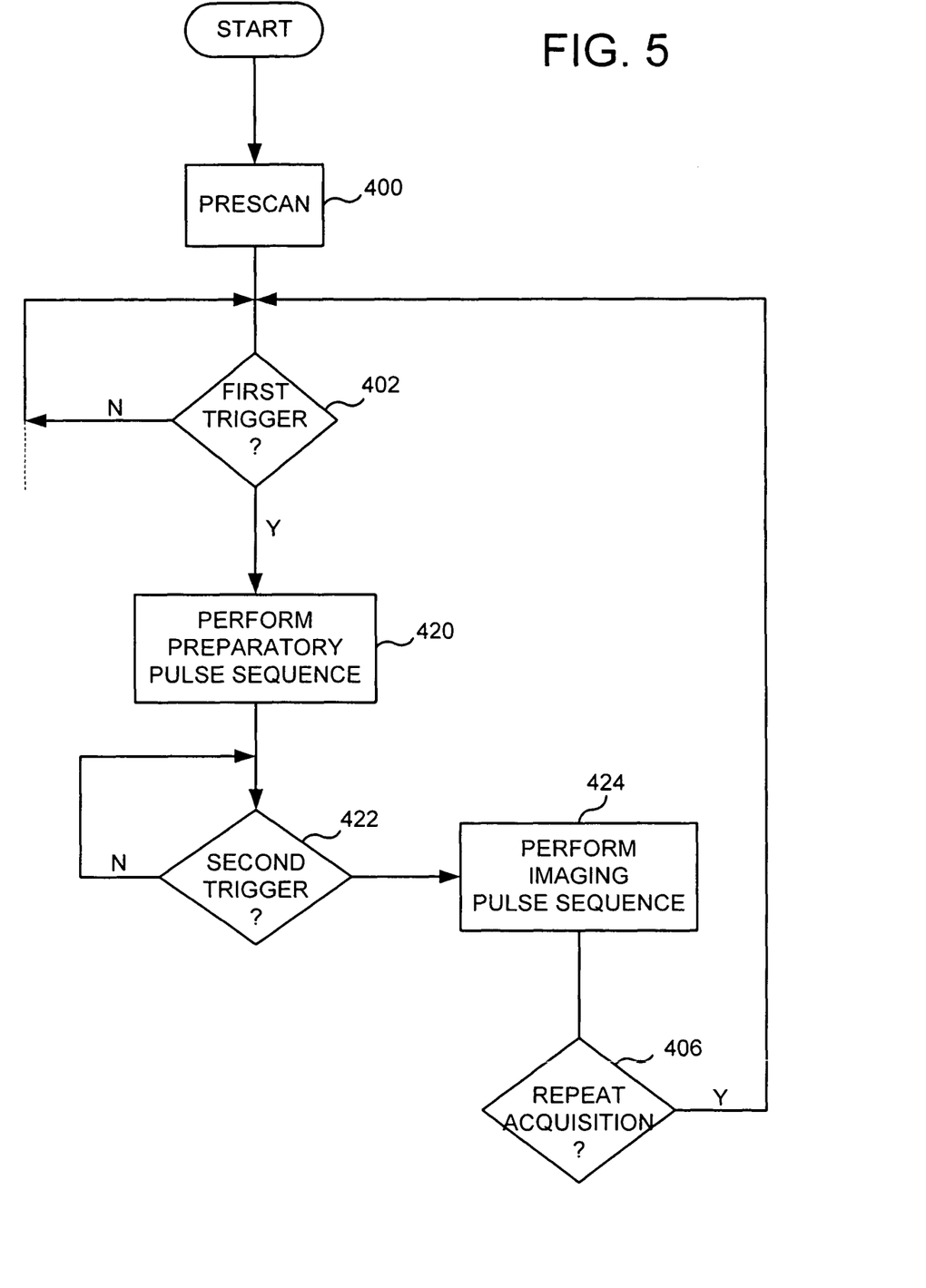
FIG. 5 is a flow chart of an alternative scan using the pulse sequence of FIG. 3.

Referring particularly to FIGS. 3 and 5, the preparatory pulse sequence is performed as described above each time the first, respiratory trigger signal is received as indicated at process block 420 to delay for the desired null time (TN). As indicated at decision block 422, the system then pauses and waits for the second, cardiac trigger signal. The heart rate is typically 8 to 10 times faster than the respiratory rate, and when the next cardiac trigger signal occurs, the image acquisition portion of the pulse sequence is initiated. As indicated at process block 424, the imaging portion of the pulse sequence described above is then performed.

Figure 1:
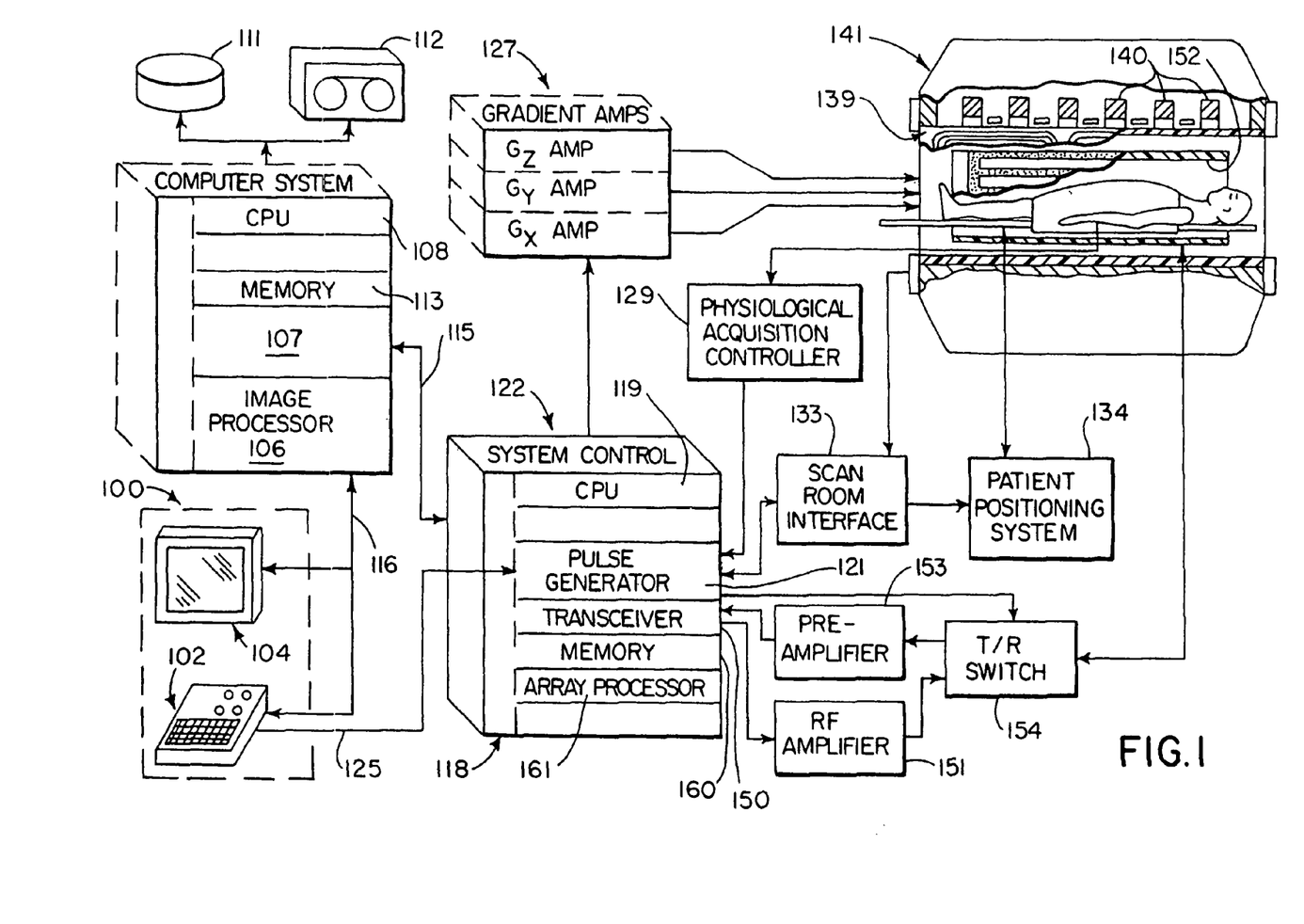
FIG. 1 is a block diagram of an MRI system which employs the present invention.

Referring to FIG. 1, there is shown the major components of a preferred MRI system which employs the present invention for in vivo imaging of human subjects. The operation of the system is controlled from an operator console 100 which includes a keyboard and control panel 102 and a display 104. The console 100 communicates through a link 116 with a separate computer system 107 that enables an operator to control the production and display of images on the screen 104. The computer system 107 includes a number of modules which communicate with each other through a backplane. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scan. The pulse generator module 121 also receives patient data from a physiological acquisition controller 129 that receives signals from a number of different sensors connected to the patient, including ECG signals from electrodes and respiratory signals from a bellows. These signals are used to produce the trigger signal described above. And finally, the pulse generator module 121 connects to a scan room interface circuit 133 which receives signals from various sensors associated with the condition of the subject and the magnet system. It is also through the scan room interface circuit 133 that a patient positioning system 134 receives commands to move the subject to the desired position for the scan.

The gradient waveforms produced by the pulse generator module 121 are applied to a gradient amplifier system 127 comprised of $G_x$, $G_y$, and $G_z$ amplifiers. Each gradient amplifier excites a corresponding gradient coil in an assembly generally designated 139 to produce the magnetic field gradients used for position encoding acquired signals. The gradient coil assembly 139 forms part of a magnet assembly 141 which includes a polarizing magnet 140 and a whole-body RF coil 152. A transceiver module 150 in the system control 122 produces pulses which are amplified by an RF amplifier 151 and coupled to the RF coil 152 by a transmit/receive switch 154. The resulting signals arising from the transverse magnetization of the excited nuclei in the subject may be sensed by the same RF coil 152 and coupled through the transmit/receive switch 154 to a preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF coil to be used in either the transmit or receive mode. To maximize SNR, we use a double loop, quadrature surface coil for both transmit and receive. In mice the coil loops have a 1 cm diameter, but because the region of interest in the brain cortex of humans is a greater distance from the surface coil, a larger diameter quadrature surface coil is employed on humans.

The NMR signals picked up by the RF coil 152 are digitized by the transceiver module 150 and transferred to a memory module 160 in the system control 122. When the scan is completed and an entire array of data has been acquired in the memory module 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the display 104.

Figure 2:
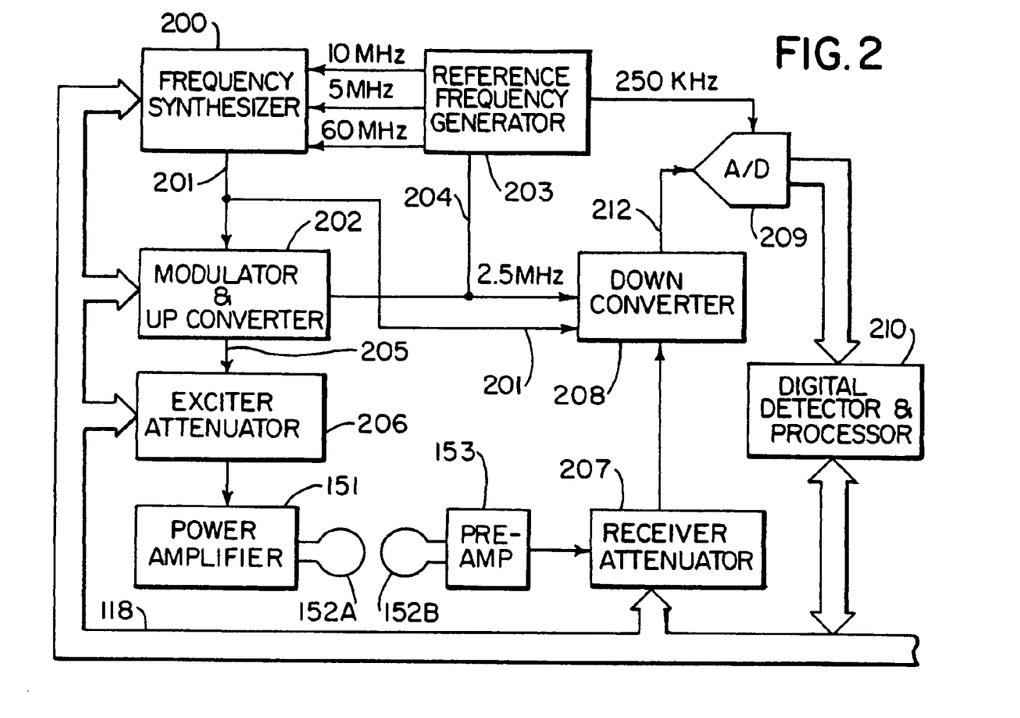
FIG. 2 is an electrical block diagram of the transceiver which forms part of the MRI system of FIG. 1.

Referring particularly to FIGS. 1 and 2, the transceiver 150 produces the RF pulses in the above pulse sequence through power amplifier 151 and coil 152A and receives the resulting NMR signals induced in the head coil 152B. As indicated above, the coils 152A and B may be separate as shown in FIG. 2, or they may be a single coil. The base, or carrier, frequency of the RF excitation field is produced under control of a frequency synthesizer 200 which receives a set of digital signals from the CPU module 119 and pulse generator module 121. These digital signals indicate the frequency and phase of the RF carrier signal produced at an output 201. The commanded RF carrier is applied to a modulator and up converter 202 where its amplitude is modulated in response to a signal R(t) also received from the pulse generator module 121. The signal R(t) defines the envelope of the RF excitation pulse to be produced and is produced in the module 121 by sequentially reading out a series of stored digital values. These stored digital values may, in turn, be changed from the operator console 100 to enable any desired RF pulse envelope to be produced.

The magnitude of the RF excitation pulse produced at output 205 is attenuated by an exciter attenuator circuit 206 which receives a digital command, from the backplane 118. The attenuated RF excitation pulses are applied to the power amplifier 151 that drives the RF coil 152A.

Referring still to FIGS. 1 and 2 the NMR signal produced by the subject is picked up by the receiver coil 152B and applied through the preamplifier 153 to the input of a receiver attenuator 207. The receiver attenuator 207 further amplifies the signal by an amount determined by a digital attenuation signal received from the backplane 118.

The received signal is at or around the Larmor frequency, and this high frequency signal is down converted in a two step process by a down converter 208 which first mixes the NMR signal with the carrier signal on line 201 and then mixes the resulting difference signal with the reference signal on line 204. The down converted NMR signal is applied to the input of an analog-to-digital (A/D) converter 209 which samples and digitizes the analog signal and applies it to a digital detector and signal processor 210 which produces 16-bit in-phase (I) values and 16-bit quadrature (Q) values corresponding to the received signal. The resulting stream of digitized I and Q values of the received signal are output through backplane 118 to the memory module 160 where they are employed to reconstruct an image.

The reference signals as well as the sampling signal are produced by a reference frequency generator 203 from a common master clock signal.

Figure 4:
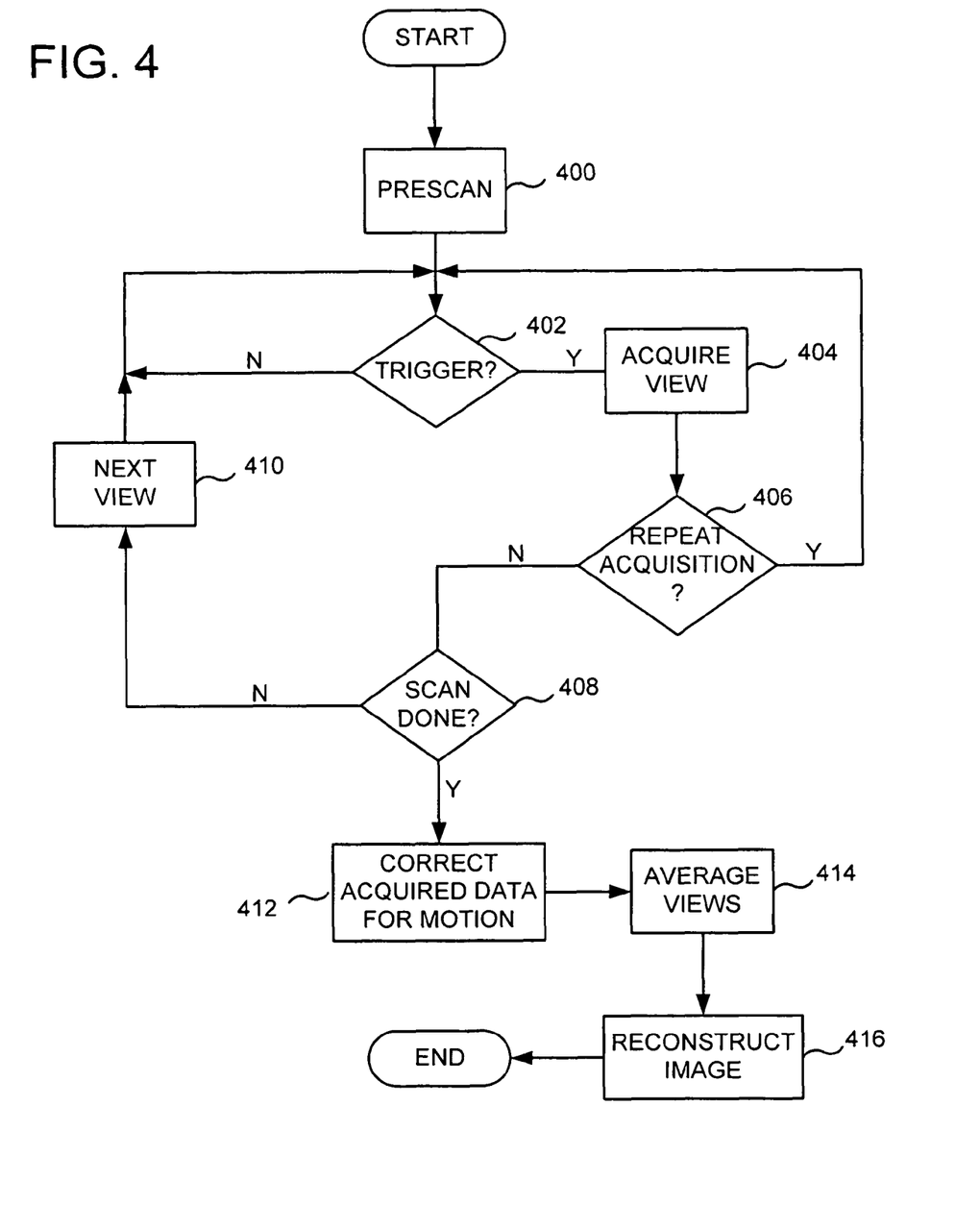
FIG. 4 is a flow chart of the steps in a scan using the pulse sequence of FIG. 3.

Referring particularly to FIG. 4, after the subject is placed in the bore of the magnet and properly aligned for a head scan, a prescan is performed as indicated at 400. The prescan acquires an image to insure proper positioning of the subject and to determine the exact larmor frequency. The system then waits for the trigger signal as indicated at decision block 402, and when the trigger occurs one view is acquired using the above-described pulse sequence of FIG. 3 as indicated at process block 404. Because of the lower polarizing field strength on commercially available scanners, a multi-NEX acquisition may be used to increase image SNR. The same phase encoding view is acquired multiple times as determined at decision block 406.

When the phase encoding view has been acquired the prescribed number of times as determined at decision block 406, a check is made at decision block 408 to determine if the scan is completed. If not, the phase encoding gradients are stepped to their next values as indicated at process block 410 and the next view is acquired when a trigger signal is produced. This process repeats until all the phase encoding views have been acquired to sample k-space in the prescribed manner.

When the data acquisition is completed, an image is reconstructed. First, each acquired view is motion corrected as indicated at process block 412. As described above, the navigation NMR signal 320 acquired with each view is used to calculate the phase corrections for each NMR echo signal 328 to offset the effects of subject motion. The multiple acquisitions of each phase encoding view are then averaged as indicated at process block 414 and an image is reconstructed from the corrected and averaged views as indicated at process block 416. As explained above, the image reconstruction is accomplished by performing a three-dimensional complex Fourier transformation along the three gradient axes and then calculating the signal magnitude at each image pixel.

Optimal performance (i.e., image quality) is obtained with this pulse sequence when the RF pulses produce the specified flip angles (90, 90, and 180 degrees for nulling, excitation, and refocusing, respectively). When the amplitude of the RF field of the transmitter coil is spatially varying across the region of interest, as occurs when using a surface coil for RF transmission, the image quality can be maintained by using RF pulses which are highly insensitive to RF field inhomogeneity, such as adiabatic RF pulses. In the preferred embodiment, adiabatic RF pulses are used in the pulse sequence to achieve substantially 90 and 180 degree rotations of the magnetization, despite using a surface coil for RF transmission. Other types of RF pulses, such as composite pulses, can alternatively be used to achieve the same effect.

To our knowledge this invention enables the first in vivo images to be acquired of individual amyloid plaques in transgenic mice without the aid of an exogenously administered contrast agent. Plaques with diameters as small as 35 µm can be successfully visualized in a living animal without a contrast agent. With the present invention one can resolve individual plaques constituting the upper 20% of the overall plaque size distribution of a two year old double transgenic mouse. Because individual plaques can be studied longitudinally over time in the same animal non-invasively, plaque biology can be studied over very long periods—i.e. the entire lifetime of an animal. Natural history studies can be performed in which the temporal and regional characteristics of plaque development are characterized. This invention may be employed to assess the effect of experimental amyloid reduction therapeutic interventions. Interesting biologic questions can be addressed, for example does a particular therapeutic approach arrest plaque growth, shrink plaques, or prevent development of new plaques? Is therapeutic modification of plaque morphology consistent across all plaques, or is there a high degree of plaque to plaque variation in response?

This invention may also be used to observe plaque biology in humans with appropriate instrumentation. Plaque sizes in human AD tissue range up to 200 µm, which is roughly twice the maximum size observed in transgenic mice. With the growing awareness of the feasibility of human imaging in ultrahigh fields ($\geq 7T$) the scan times can be shortened while maintaining high SNR and some of the same applications can be envisioned in humans as in transgenic mice.

While the preferred embodiment of the invention is used to image amyloid plaque in Alzheimer's patients, it should be apparent to those skilled in the art that other clinical or research applications are also possible. For example, the invention may be employed to image tumor micro architecture for use in biological research or for assessing the effects of therapeutic intervention. The invention may also be used to image vascular microstructures for use in research and diagnosis of vascular diseases leading to stroke, renovascular disease, or cardiac disease. The invention may be used in contrast enhanced imaging to label specific tissues, molecules, cells or other microstructures. For example, the invention may be used to image labeled stem cells to track cell and organ development over time.

The invention claimed is:

1. A method for acquiring an in vivo, high resolution magnetic resonance image from a subject, the steps comprising:
   a) producing a trigger signal when the subject is in a preselected phase of the subject's respiratory cycle;
   b) performing a pulse sequence to acquire an NMR signal when the trigger signal is produced, the pulse sequence including:
      b)i) performing a preparatory pulse sequence to create uniform view-to-view longitudinal magnetization in the presence of non-uniform view-to-view trigger times in which the longitudinal magnetization in a region of interest in the subject is set to a preset amount by applying an rf nulling pulse with a substantially 90° flip angle followed by a preset null recovery time (TN);
      b)ii) producing transverse magnetization in the region of interest by applying an rf excitation pulse after step b)i);
      b)iii) producing an NMR echo signal at a preselected time (TE) after application of the rf excitation pulse;
      b)iv) acquiring the NMR echo signal in the presence of a readout magnetic field gradient;
   c) changing a magnetic field gradient in the pulse sequence and repeating step b) to acquire another NMR signal; and
   d) repeating step c) until sufficient NMR echo signals are acquired to reconstruct an image.

2. The method as recited in claim 1 in which the region of interest is in the subject's brain.

3. The method as recited in claim 2 in which the region of interest is in a portion of the subject's brain containing amyloid plaque and the NMR echo signal is produced in step b)iii) by producing an rf refocusing pulse.

4. The method as recited in claim 1 in which the rf nulling and rf excitation pulses are adiabatic half-passage RF pulses that flip substantially all of the longitudinal magnetization into the transverse plane.

5. The method as recited in claim 1 in which the pulse sequence performed in step b) further includes:
   producing a first selective RF refocusing pulse in the presence of a first gradient after step b)ii) to refocus the transverse magnetization in a first slice through the region of interest; and
   producing a second selective RF refocusing pulse in the presence of a second gradient after step b)ii) to refocus the transverse magnetization in a second slice through the region of interest.

6. The method as recited in claim 5 in which the selective RF refocusing pulses are hyperbolic scant type pulses.

7. A method for acquiring an in vivo, high resolution magnetic resonance image from a subject, the steps comprising:
   a) producing a first trigger signal when the subject is in a preselected phase of the subject's respiratory cycle;
   b) performing a preparatory pulse sequence when the first trigger signal is produced by applying an rf nulling pulse followed by a preset null recovery time (TN);
   c) producing a second trigger signal when the subject is in a preselected phase of the subject's cardiac cycle;
   d) performing an imaging pulse sequence to acquire an NMR echo signal from a selected region of interest in the subject after the second trigger signal is produced; and
   e) repeating steps a) through d) until sufficient NMR echo signals are acquired to reconstruct an image.

8. The method as recited in claim 7 in which the rf nulling pulse has a substantially 90° flip angle.

9. The method as recited in claim 7 in which step d) includes:
   d)i) producing transverse magnetization in the region of interest by applying an rf excitation pulse;
   b)ii) producing an NMR echo signal at a preselected time (TE) after application of the rf excitation pulse; and
   d)iii) acquiring the NMR echo signal in the presence of a readout magnetic field gradient.

10. The method as recited in claim 9 in which the region of interest is in a portion of the subject's brain containing amyloid plaque and the NMR echo signal is produced in step d)ii) by producing an rf refocusing pulse.

11. The method as recited in claim 10 in which step d) further includes:

producing a first selective RF refocusing pulse in the presence of a first gradient after step d)i) to refocus the transverse magnetization in a first slice through a region of interest; and producing a second selective RF refocusing pulse in the presence of a second gradient after step d)i) to refocus the transverse magnetization in a second slice through the region of interest.

\* \* \* \* \*

UNITED STATES PATENT AND TRADEMARK OFFICE
CERTIFICATE OF CORRECTION

PATENT NO. : 9,320,452 B2
APPLICATION NO. : 11/631581
DATED : April 26, 2016
INVENTOR(S) : Michael G. Garwood et al.

It is certified that error appears in the above-identified patent and that said Letters Patent is hereby corrected as shown below:

In the Claims

Column 10, line 34 "scant" should be -- secant --

Signed and Sealed this
Second Day of August, 2016

Michelle K. Lee
*Director of the United States Patent and Trademark Office*